United States Patent [19]

Gschwend et al.

[11] 4,025,505

[45] May 24, 1977

[54] AROMATIC DICARBOXAMIDES

[75] Inventors: Heinz Werner Gschwend, New Providence, N.J.; Malvin Jason Hillman, Liverpool, N.Y.

[73] Assignee: Ciba-Geigy Corporation, Ardsley, N.Y.

[22] Filed: Nov. 13, 1975

[21] Appl. No.: 631,789

Related U.S. Application Data

[63] Continuation-in-part of Ser. No. 547,063, Feb. 4, 1975, abandoned, which is a continuation-in-part of Ser. No. 449,872, March 11, 1974, Pat. No. 3,941,883.

[52] U.S. Cl. .................. 260/239.3 B; 260/281 R; 260/295 M; 260/326 R; 260/332.2 C; 260/332.2 H; 260/346.7; 260/347.3; 260/470; 260/515 A; 260/516; 260/558 D; 260/578; 424/256

[51] Int. Cl.² ...................................... C07D 209/00

[58] Field of Search ....... 260/326 N, 326 S, 281 R, 260/239.3 B

[56] References Cited

UNITED STATES PATENTS

| | | | |
|---|---|---|---|
| 3,442,938 | 5/1969 | Christensen et al. | 260/326 N |
| 3,898,214 | 8/1975 | Vogt | 260/239.3 B |
| 3,941,883 | 3/1976 | Gschwend et al. | 260/326 N |
| 3,946,017 | 3/1976 | Schefczik et al. | 260/281 R |

FOREIGN PATENTS OR APPLICATIONS

| | | | |
|---|---|---|---|
| 1,274,142 | 5/1972 | United Kingdom | |
| 901,420 | 7/1962 | United Kingdom | 260/326 N |
| 1,241,469 | 8/1971 | United Kingdom | |
| 1,241,470 | 8/1971 | United Kingdom | |

*Primary Examiner*—Ethel G. Love
*Attorney, Agent, or Firm*—Joseph G. Kolodny; Theodore O. Groeger; John J. Maitner

[57] ABSTRACT

N-(4-aminophenyl)-aromatic dicarboximides, e.g. those of the formula

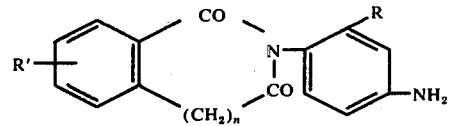

R = alkyl, (hydroxy, alkoxy, alkylmercapto,-sulfinyl or -sulfonyl)-alkyl, halogeno or $CF_3$ R' = alkyl, alkoxy, alkylmercapto, -sulfinyl or -sulfonyl, halogeno, $CF_3$, COOH, CN carbamoyl or sulfamoyl; n=0 or 1 or salts thereof are anticonvulsants.

7 Claims, No Drawings

AROMATIC DICARBOXAMIDES

CROSS REFERENCE TO RELATED APPLICATIONS

This is a continuation-in-part of application Ser. No. 547,063, filed Feb. 4, 1975 (now abandoned) which in turn is a continuation-in-part of application Ser. No. 449,872, filed Mar. 11, 1974, (now Pat. 3,941,883).

BACKGROUND OF THE INVENTION

Compounds of the above formula, wherein at least one of R and R' is hydrogen, are disclosed in U.S. Pat. No. 3,767,805 or British Pat. No. 901,420 as intermediates in the preparation of "α-(cyclic tert. aminophenyl)-aliphatic acids" or "azo colouring matters" respectively. Surprisingly it was found that by properly selecting substituents and their relative positions within the aromatic nuclei of said dicarboximides, highly potent anticonvulsant agents are obtained.

SUMMARY OF THE INVENTION

The present invention concerns and has for its object the provision of novel N-(4-aminophenyl)-aromatic dicarboximides, more particularly of those corresponding to Formula I

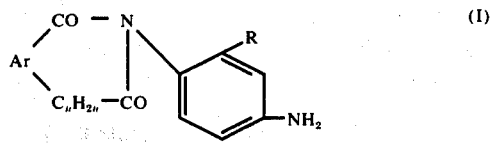

wherein Ar is 1,2-phenylene substituted by one member selected from lower alkyl, alkoxy, alkylmercapto, -sulfinyl or -sulfonyl, halogeno, $CF_3$, carboxy, carbalkoxy, CN, carbamoyl, sulfamoyl, mono- or dialkylcarbamoyl or -sulfamoyl; unsubstituted, lower alkylated or halogenated 2,3- or 3,4-(furylene, thienylene or pyridylene), R is lower alkyl, (hydroxy, alkoxy, alkylmercapto, -sulfinyl or -sulfonyl)-alkyl, halogeno or trifluoromethyl, $n$ is an integer from 0 to 3 and $C_nH_{2n}$ separates Ar from CO by one or no carbon atom, or pharmaceutically acceptable salts thereof, and of corresponding pharmaceutical compositions and of methods for the preparation and application of these products, which are useful anticonvulsant agents, for example in the treatment or management of epilepsy or other spastic conditions.

DESCRIPTION OF THE PREFERRED EMBODIMENTS

The 1,2-phenylene radical Ar, is preferably substituted by one member selected from the group consisting of methyl, ethyl, n- or i-propyl or -butyl; methoxy, ethoxy, n- or i-propoxy or -butoxy; (methyl or ethyl)-(mercapto, sulfinyl or sulfonyl); fluoro, chloro or bromo; trifluoromethyl; cyano; carbamoyl, sulfamoyl, mono- or di-(methyl or ethyl)-(carbamoyl or sulfamoyl). The 2,3- or 3,4-(furylene, thienylene or pyridylene) radicals Ar are preferably unsubstituted, or may contain, for example, one member selected from the group consisting of methyl, ethyl, fluoro or chloro.

The lower alkyl group or halogen atom R is preferably methyl, ethyl, fluoro, chloro or bromo but also one of the other respective members listed above, and the substituted lower alkyl group R is preferably α-(hydroxy, methoxy, ethoxy, methyl- or ethylmercapto, -sulfinyl or -sulfonyl)-(methyl or ethyl). The term "lower", referred to above and hereinafter in connection with organic radicals or compounds respectively, defines such with up to 7, preferably up to 4, especially up to 2 carbon atoms.

The above mentioned salts of the amines of Formula I are preferably those of the therapeutically useful acids listed below.

The compounds of the invention exhibit valuable pharmacological properties, primarily anticonvulsant activity, as can be demonstrated in animal tests, using advantageously mammals, such as mice or rats, as test objects. Said compounds can be applied to the host suffering from agitation and/or convulsions either enterally or parenterally, e.g. orally or intraperitoneally, for example in the form of aqueous solutions or starchy suspensions. The oral or intraperitoneal dosage may range between about 1 and about 800 mg/kg/day, preferably between about 5 and 500 mg/kg/day or especially between about 10 and about 50 mg/kg/day. Anticonvulsant effects are observed, for example, by the protection of said mammals against electrically or chemically induced seizures, such as mouse or rat minimum or maximum electroshock, or seizures caused by 1,5-pentamethylenetetrazole, picrotoxin, thiosemicarbazide or strychnine. According to the former test the compounds of the invention, for example, the N-(4-amino-o-tolyl)-4-chlorophthalimide, an illustrative member thereof, are administered to the animals either orally or intraperitoneally and one or two hours later, preferably at peak effect, they are given an electric shock, e.g. to mize 50 milliamperes of current and 0.2 second duration through corneal electrodes, from which all animals recover. Those animals not exhibiting a tonic (hind limb) extensor seizure are considered protected.

They are also given the compounds of the invention, either orally or intraperitoneally, and one hour later, for example, 24 mg/kg 1,5-pentamethylenetetrazole intravenously to rats. They are checked immediately for the presence of clonic seizures and all animals not exhibiting them are also considered protected. Furthermore, the overt effects of the compounds of Formula I are observed in rats ½, 1,2 and 20 hours after various oral or intraperitoneal doses and $ED_{50}$ values are estimated for various effects, e.g. muscle tone or ataxia, indicating skeletal muscle relaxing activity. According to the test results observed, the compounds of the invention are useful anticonvulsant agents, for example in the treatment or management of epilepsy or other spastic conditions. They are also useful intermediates in the preparation of other valuable products, preferably of pharmacologically active compounds, e.g. related anti-inflammatory agents.

Preferred compounds of the invention are those of Formula I, wherein Ar is 1,2-phenylene substituted by one member selected from the group consisting of lower alkyl, alkoxy, alkylmercapto, -sulfinyl or -sulfonyl, halogeno, trifluoromethyl, carboxy, carbalkoxy, cyano, carbamoyl, sulfamoyl, mono- or dialkylcarbamoyl or -sulfamoyl, unsubstituted, or mono- lower alkylated or halogenated 2,3- or 3,4-(furylene, thienylene or pyridylene), R is lower alkyl, lower α-(hydroxy, alkoxy, alkylmercapto, -sulfinyl or -sulfonyl)-alkyl, halogeno or trifluoromethyl and n is the integer 0 or 1, or a therapeutically acceptable alkali metal or acid addition salt thereof.

More preferred on account of said effects are those compounds of Formula I, wherein Ar is 1,2-phenylene substituted by one member selected from the group consisting of methyl, ethyl, methoxy, ethoxy, (methyl or ethyl)-(mercapto, sulfinyl or sulfonyl), fluoro, chloro, bromo, trifluoromethyl, carboxy, carbomethoxy, cyano, carbamoyl, sulfamoyl, mono or di-(methyl or ethyl)-(carbamoyl or sulfamoyl); unsubstituted or mono-(methyl, ethyl, fluoro or chloro)-substituted 2,3- or 3,4-(furylene, thienylene or pyridylene), R is methyl ethyl, fluoro, chloro, bromo, trifluoromethyl or α-(hydroxy, methoxy, ethoxy, methyl- or ethylmercapto, -sulfinyl or -sulfonyl)-(methyl or ethyl) and $n$ is the integer 0 or 1, or a therapeutically acceptable acid addition salt thereof.

Outstanding activity is exhibited by compounds of Formula II

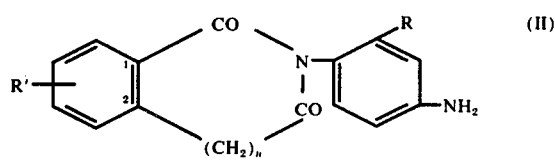

wherein R is methyl or ethyl, R' is methyl, methoxy, methylmercapto, -sulfinyl or -sulfonyl, fluoro, chloro, bromo, trifuoromethyl, carboxy, cyano, carbamoyl or dimethylcarbamoyl, preferably in the 4- or 5- positions, and $n$ is the integer 0 or 1, or a therapeutically acceptable acid addition salt thereof.

Of special value are those compounds of Formula II, wherein R is methyl, R' is methyl, fluoro, chloro, bromo or trifluoromethyl, preferably in the 4-position, and $n$ is zero, or a therapeutically acceptable acid addition salt thereof.

The compounds of the invention are prepared according to methods known per se. For example, they are obtained by reducing a compound of Formula III

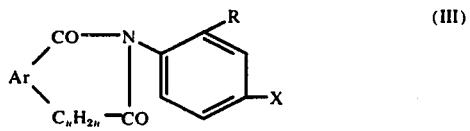

wherein X is a nitro, azido or azo group and, if desired, converting any resulting compound into another compound of the invention.

An azo group X is preferably derived from an isocyclic aromatic radical, e.g. phenyl, or H-Ar. Preferred radicals X are: $NO_2$, $N_3$ and $C_6H_5-N_2$. They are converted into amino by conventional reduction, for example, with the use of catalytically activated or nascent hydrogen, e.g. hydrogen in the presence of platinum, palladium or nickel catalysts, e.g. Raney nickel, or generated by the action of non-precious metals, e.g. zinc or iron, on acids, such as mineral acids, e.g. hydrochloric or sulfuric acid, or with the use of reducing agents, preferably salts of elements of the 4th to 6th group of the Periodic Table and being in a low oxidation state, such as titanous, stannous or chromous halides, ammonium polysulfides or alkali metal hydrosulfites.

Another process for the preparation of the compounds of this invention consists in hydrolyzing a compound of Formula III, wherein X is an isocyanato or acylamino group and, if desired, converting any resulting compound into another compound of the invention.

An acylamino group is preferably derived from a lower alkanoic or aralkanoic acid or carbonic acid half-ester containing as aromatic radical either phenyl or H-Ar. Preferred radicals X are NCO, $C_mH_{2m+1}$—CONH, $C_mH_{2m+1}$—OCONH, $C_6H_5$—CONH or $C_6H_5CH_2OCONH$, wherein $m$ is 1 to 7. These acylated amino groups are converted into amino by acidic or basic hydrolysis, the isocyanato group (for example formed in the course of the Schmidt-reaction) preferably with strong inorganic acids, such as hydrochloric, sulfuric or phosphoric acid, and the other acylamino groups preferably with the use of aqueous bases, such as aqueous alkali metal hydroxides or carbonates, or quaternary ammonium hydroxides, e.g. sodium hydroxide, potassium carbonate or trimethylbenzylammonium hydroxide. Care should be taken in said hydrolysis, in order to prevent the hydrolytic opening of the imide moiety.

The compounds of the invention so obtained can be converted into each other according to methods known per se. For example, resulting hydroxyalkyl compounds, preferably acid addition salts thereof, can be etherified with lower alkyl halides or sulfates to corresponding compounds of Formula I, wherein R is lower alkoxyalkyl. Moreover, resulting alkylmercapto-products can be oxidized, advantageously with the use of alkali metal periodates or perbenzoic acid, to yield corresponding alkylsulfinyl or -sulfonyl compounds, or carbamoyl or sulfamoyl-products may either be treated under strong alkaline conditions with said esters of lower alkanols, to yield the N-alkylated derivatives thereof, or the former with dehydrating agents, e.g. phosphorus oxychloride, to yield cyanides, and any cyanides may be hydrolyzed to carbamoyl compounds with said strong acids.

A resulting compound containing carboxy can be converted into a metal salt, such as an alkali metal, e.g. sodium salt, or a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicyclic, aminosalicylic, pamoic, nicotinic, methanesulfonic, ethanesulfonic, hydroxy-ethanesulfonic, ethylenesulfonic, benzenesulfonic, halogen-benzenesulfonic, toluenesulfonic, naphthalenesulfonic, sulfanilic, or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example by separation of diasteromeric salts thereof, e.g. by the fractional crystallization of d- or l-tartrates.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. As mentioned above, isocyanates are formed from the corresponding acid azides and acylamino compounds may be formed in the formation of the cyclic starting materials from their acyclic precursors. In the process of the invention, those starting materials are advantageously selected, which yield the above-described preferred embodiments of the invention, especially those corresponding to Formula II.

The starting material used in known or, if new, can be prepared according to the methods described for known analogs thereof, or by the methods illustrated in the examples herein.

The pharmacologically active compounds of the invention are useful in the manufacture of pharmaceutical compositions containing an effective amount thereof in conjunction or admixture with excipients suitable for either enteral, e.g. oral, or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centigrade, all parts wherever given are parts by weight, and all evaporations are carried out under reduced pressure.

EXAMPLE 1

The mixture of 3.94 g of N-(4-nitro-o-tolyl)-3-methylphthalimide, 200 ml of ethyl acetate and 2.2 g of Raney nickel (pre-washed with water and ethyl acetate) is hydrogenated at 3.1 atm. and room temperature until the hydrogen uptake ceases. It is filtered, evaporated, the residue triturated with chloroform, filtered again, the filtrate evaporated and the residue recrystallized from methanol, to yield the N-(4-amino-o-tolyl)-3-methylphthalimide of the formula

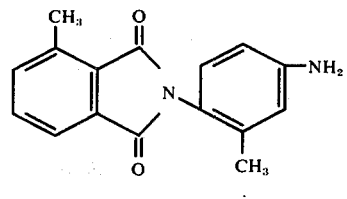

melting at 209°–211°.

The starting material is prepared as follows: The mixture of 16.2 g of 3-methylphthalic anhydride, 15.2 g of 4-nitro-o-toluidine and 400 ml of xylene is refluxed for 2 days and evaporated. The residue is taken up in 400 ml of acetic anhydride and the mixture refluxed for 18 hours. It is evaporated and the residue recrystallized from ethanol, to yield the N-(4-nitro-o-tolyl)-3-methylphthalimide, melting at 195°–199°.

EXAMPLE 2

The mixture of 4.28 g of N-(4-nitro-o-tolyl)-4-methylphthalimide, 200 ml of 95% aqueous ethanol and 0.21 g of 5% palladium on charcoal is hydrogenated at 3.1 atm and 45° until the hydrogen uptake ceases. The resulting suspension is diluted with the minimum amount of dimethylformamide to solubilize the organic material, filtered and evaporated. The residue is taken up in chloroform, the mixture filtered, evaporated and the residue recrystallized from methanol, to yield the N-(4-amino-o-tolyl)-4-methylphthalimide melting at 144°–147°.

The starting material is prepared as follows: The mixture of 5.0 g of 4-methylphthalic anhydride, 4.7 g of 4-nitro-o-toluidine and 100 ml of xylene is refluxed for 2 ½ days on a water trap. It is evaporated and the residue recrystallized from ethanol, to yield the N-(4-nitro-o-tolyl)-4-methylphthalimide melting at 184°–186°.

EXAMPLE 3

The mixture of 1.65 g of N-(4-nitro-o-tolyl)-3-chlorophthalimide, 200 ml of ethyl acetate and 0.92 g of pre-washed Raney nickel is hydrogenated at 3.1 atm. and room temperature until the hydrogen uptake ceases. It is filtered, evaporated and the residue recrystallized from methanol, to yield the N-(4-amino-o-tolyl)-3-chlorophthalimide melting at 209°–211°.

The starting material is prepared as follows: The mixture of 3.0 g of 3-chlorophthalic anhydride, 2.5 g of 4-nitro-o-toluidine and 200 ml of xylene is refluxed for 2 days on a water-trap and evaporated. The residue is taken up in chloroform, the mixture filtered, the filtrate chromatographed on silica gel and the column eluted with chloroform-ethyl acetate (9:1), to yield the N-(4-nitro-o-tolyl)-3-chlorophthalimide melting at 229°–232°.

EXAMPLE 4

The mixture of 12.4 g of N-(4-nitro-o-tolyl)-4-chlorophthalimide, 1.0 lt. ethyl acetate and 10 ml of an ethanolic suspension containing 6.9 g of Raney nickel is hydrogenated at 2.8 atm. and room temperature for 12 hours. It is filtered, concentrated to about half of its original volume and the precipitate formed collected, to yield the N-(4-amino-o-tolyl)-4-chlorophthalimide melting at 201°–203°. Its 4-bromo-analog melts at 208°–211°.

The starting material is prepared as follows: The mixture of 36 g of 4-chlorophthalic acid and 250 ml of acetic anhydride is refluxed for 2 hours and evaporated. The residual 4-chlorophthalic anhydride is dried in a high vacuum and 27.8 g thereof refluxed in 480 ml of toluene together with 23.1 g of 4-nitro-o-toluidine for 1 day. It is cooled, the precipitate filtered off, washed with benzene and dried at 80°/0.1 mmHg, to yield the corresponding amide melting at 185°–188°.

The mixture of 35 g thereof and 250 ml of acetic anhydride is refluxed for 2 hours and evaporated. The residue is dried, taken up in the minimum amount of hot ethyl acetate, the solution treated with charcoal, filtered, the filtrate cooled and the precipitate formed collected, to yield N-(4-nitro-o-tolyl)-4-chlorophthalimide melting at 221°–222°.

EXAMPLE 5

The mixture of 2.3 g of N-(4-nitro-2-chlorophenyl)-4-chlorophthalimide, 220 ml of ethyl acetate and 1 g of Raney nickel is hydrogenated at room temperature and 3.1 atm. pressure until the hydrogen uptake ceases. It is filtered, evaporated and the residue recrystallized from methanol, to yield the N-(4-amino-2-chlorophenyl)-4-chlorophthalimide melting at 198°–201°.

The starting material is prepared as follows: The mixture of 3.0 g of 4-chlorophthalic anhydride, 2.8 g of 4-nitro-2-chloroaniline and 30 ml of acetic acid is refluxed for 24 hours. It is cooled, the precipitate formed filtered off and washed with diethyl ether, to yield the N-(4-nitro-2-chlorophenyl)-4-chlorophtalimide melting at 209°–212°.

EXAMPLE 6

The mixture of 10.0 g of N-(4-nitro-o-tolyl)-4-fluorophthalimide, 500 ml of ethyl acetate and 5 g of Raney nickel is hydrogenatd at 3.1 atm. and room temperature until the hydrogen uptake ceases. It is filtered, evaporated, and the residue recrystallized from ethanol, to yield the N-(4-amino-o-tolyl)-4-fluorophthalimide, melting at 180°–182°.

The starting material is prepared as follows: The mixture of 6,8 g of 4-fluorophthalic anhydride, 6.2 g of 4-nitro-o-toluidine and 160 ml of xylene is refluxed for 4 days at a water trap. It is evaporated, the residue taken up in 150 ml of acetic anhydride and the solution refluxed for 5 hours. It is evaporated and the residue recrystallized from n-propanol, to yield the N-(4-nitro-o-tolyl)-4-fluorophthalimide melting at 166°–168.5°.

EXAMPLE 7

The mixture of 3.55 g of N-(4-nitro-o-tolyl)-4-trifluoromethylphthalimide, 200 ml of 95% aqueous ethanol and 0.18 g of 5% palladium on carbon is hydrogenated at 3.1 atm. and 45° until the hydrogen uptake ceases. It is filtered, evaporated and the residue recrystallized from ethanol, to yield the N-(4-amino-o-tolyl)-4-trifluoromethylphthalimide melting at 161°–163°.

The starting material is prepared as follows: The mixture of 13.0 g of 4-trifluoromethylphthalic anhydride, 3.16 g of 4-nitro-o-toluidine and 100 ml of xylene is refluxed for 2 ½ days at a water trap. It is evaporated and the residue recrystallized from ethanol, to yield the N-(4-nitro-o-tolyl)-4-trifluoromethylphthalimide melting at 156°–158°.

EXAMPLE 8

The mixture of 2.83 g of N-(4-nitro-o-tolyl)-pyridine-2,3-dicarboximide, 200 ml of ethyl acetate and 1.6 g of prewashed Raney nickel is hydrogenated at 3.1 atm. and room temperature until the hydrogen uptake ceases. It is filtered, evaporated, the residue taken up in chloroform, the solution treated with charcoal, filtered, evaporated and the residue recrystallized from methanol, to yield the N-(4-amino-o-tolyl)-pyridine-2,3-dicarboximide of the formula

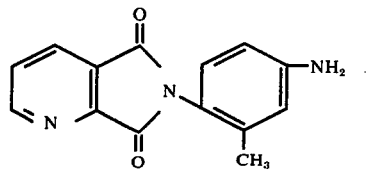

melting at 180°–182°.

The starting material is prepared as follows: The mixture of 10.0 g of pyridine-2,3-dicarboxylic anhydride, 10.3 g of 4-nitro-o-toluidine and 250 ml of xylene is refluxed for 2 days. It is evaporated, the residue taken up in 250 ml of acetic anhydride and the mixture refluxed for 5 hours. It is evaporated, the residue triturated with hot ethanol and the insoluble material recrystallized from ethyl acetate, to yield the N-(4-nitro-o-tolyl)-pyridine-2,3-dicarboximide melting at 223°–225°.

EXAMPLE 9

The mixture of 6.0 g of N-(4-nitro-o-tolyl)-4methylmercaptophthalimide, 3.0 g of Raney nickel and 200 ml of ethyl acetate is hydrogenated at 3.1 atm. and room temperature until the hydrogen uptake ceases. It is diluted with dimethylformamide to solubilize any organic material, filtered and the filtrate evaporated. The residue is recrystallized from chloroform-diethyl ether to yield the N-(4-amino-o-tolyl)-4-methylmercaptophthalimide melting at 173°–177°. The starting matrial is prepared as follows: The mixture of 8.5 g of potassium methylsulfide, 21.2 g of diethyl 4-chlorophthalate and 100 ml of dimethylformamide is stirred at 100°–120° for one week. After cooling it is diluted with diethyl ether, the precipitate filtered off, the filtrate washed with 5% aqueous sodium hydroxide, water, dried and evaporated, to yield the diethyl 4-methylmercaptophthalate. The mixture of 18.2 g thereof and 100 ml of 30% aqueous ethanolic sodium hydroxide is refluxed for 2 ½ hours and evaporated. The residue is acidified with concentrated hydrochloric acid and thoroughly extracted with diethyl ether. The extract is washed with water, dried, evaporated and the residue recrystallized from 30% aqueous methanol, to yield the 4-methylmercaptophthalic acid, m.p. 178°–181°. The mixture of 13.0 g thereof and 130 ml of acetic anhydride is refluxed for 3 hours and evaporated, to yield the 4-methylmercaptophthalic anhydride melting at 157°–160°. The mixture of 10.3 g thereof, 7.8 g of 4-nitro-o-toluidine and 100 ml of acetic acid is refluxed for 24 hours and evaporated. The residue is recrystallized from ethanol-ethyl acetate to yield the N-(4-nitro-o-tolyl)-4-methylmercaptophthalimide melting at 155°–157°.

EXAMPLE 10

The stirred solution of 2.8 g of N-(4-amino-o-tolyl)-4-methylmercaptophthalimide in 70 ml of dioxane and 70 ml of methanol is treated dropwise with the solution of 2.94 g of sodium periodate in the minimum amount of water, and stirring is continued at room temperature for one week. The mixture is diluted with ethyl acetate, the resulting precipitate removed by filtration, the filtrate washed with water, dried and evaporated. The residue is triturated with 2N hydrochloric acid, filtered off and dried, to yield the N-(4-amino-o-tolyl)-4-methylsulfinylphthalimide hydrochloride melting at 185°–195° with decomposition.

EXAMPLE 11

The mixture of 2.5 g of N-(4- nitro-o-tolyl)-4-methylsulfonylphthalimide, 0.1 g of palladium on carbon, 80 ml of dimethylformamide and 200 ml of ethyl acetate is hydrogenated at 2.7 atm. and room temperature until the hydrogen uptake ceases. It is filtered, the filtrate extracted with hydrochloric acid, washed with ethyl acetate, basified with sodium carbonate, reextracted with ethyl acetate, the organic solution washed with water, dried filtered and evaporated. The residue is triturated with ethyl acetate-diethyl ether, to yield the N-(4-amino-o-tolyl)-4-methylsulfonylphthalimide melting at 214°–220°.

The starting material is prepared as follows: The suspension of 3.8 g of N-(4-nitro-o-tolyl)-4-methylmercaptophthalimide, in 40 ml of glacial acetic acid is treated dropwise with 8 ml of 30% hydrogen peroxide at 80° while stirring. After 4 hours the mixture is diluted with water, the precipitate filtered off, washed with water and dryed, to yield the N-(4-nitro-o-tolyl)-4-methylsulfonylphthalimide melting at 239°–245°.

EXAMPLE 12

The mixture of 6.5 g of N-(4-nitro-o-tolyl)-4-dimethylcarbamoylphthalimide, 3.0 g of Raney nickel and 270 ml of ethyl acetate is hydrogenated at 3.1 atm. and room temperature until the hydrogen uptake ceases. It is filtered, the filtrate evaporated, the residue washed with hot ethanol and dried, to yield the N-(4-amino-o-tolyl)-4-dimethylcarbamoylphthalimide melting at 214°–217°.

The starting material is prepared as follows: To the solution of 17.6 g of trimellitic anhydride acid chloride in 120 ml of benzene, that of 7.9 g of dimethylamine in 4.8 g of pyridine and 40 ml of benzene is added and the mixture stirred overnight. It is filtered and evaporated to give the corresponding dimethylamide.

The mixture of 14.0 g thereof, 9.6 g of 4-nitro-o-toluidine and 200 ml of xylene is refluxed for 2 days and evaporated. The residue is taken up in 200 ml of acetic anhydride, the mixture refluxed for 3 hours and again evaporated. The residue is recrystallized from methanol-diethyl ether to yield the N-(4-nitro-o-tolyl)-4-dimethylcarbamoylphthalimide melting at 184°–188°.

EXAMPLE 13

The mixture of 3.0 g of N-(4-nitro-2-methylmercaptomethylphenyl)-4-chlorophthalimide, 1.5 g of Raney nickel and 250 ml of ethyl acetate is hydrogenated at room temperature and atmospheric pressure until the hydrogen uptake ceases. It is filtered, the filtrate evaporated and the residue recrystallized from benzene, to yield the N-(4-amino-2-methylmercaptomethylphenyl)-4-chlorophthalimide melting at 134°–137°. Analogously the N-(4-amino-2-methylsulfonylmethylphenyl)-4-chlorophthalimide is prepared, m.p. 253°–257° (acetonitrile); as well as the N-(4-amino-2-hydroxymethylphenyl)-4-chlorophthalimide, m.p. 228°–230° (ethyl acetatediethyl ether).

The starting materials are prepared as follows: The solution of 23.4 g of t-butylhypochlorite in 20 ml of methylene chloride is added to that of 30.0 g of 4-nitroaniline and 27.0 g of dimethyl thioether in 650 ml of acetonitrile and 200 ml of methylene chloride while stirring at −40° under nitrogen. After 4 hours the temperature is raised to −20° and maintained there for three hours. After the addition of 30 g of sodium methoxide in 100 ml of methanol the mixture is refluxed for 15 hours, cooled, filtered and evaporated. The residue is dissolved in diethyl ether and filtered through a silica gel column to remove any unreacted 4-nitroaniline as its benzenesulfonate following addition of 17.4 g of benzenesulfonic acid. The filtrate is evaporated and the residue recrystallized from ethanol, to yield the 4-nitro-2-methylmercaptomethylaniline melting at 72°–77°.

The mixture of 9.3 g thereof, 8.6 g of 4-chlorophthalic anhydride and 200 ml of acetic acid is refluxed for 18 hours and evaporated. The residue is decolorized in diethyl ether with the aid of carbon, the mixture filtered and the filtrate concentrated to afford the N-(4-nitro-2-methylmercaptomethylphenyl)-4-chlorophthalimide melting at 112°–115°.

The solution of 1.8 g thereof in 10 ml of acetic acid is treated dropwise with 3 ml of 30% hydrogen peroxide while stirring at 70°–80°. After 3 hours the mixture is cooled, diluted with water, filtered and dried, to yield the N-(4-nitro-2-methylsulfonylmethylphenyl)-4-chlorohthalimide which does not melt under 250°.

The mixture of 1.5 g of N-(4-nitro-2-methylmercaptomethylphenyl)-4-chlorophthalimide and 50 ml of methyl iodide is refluxed for 6 days in the absence of light and evaporated. The residue is taken up in hot benzene, the mixture filtered and evaporated to yield the N-(4-nitro-2-iodomethylphenyl)-4-chlorophthalimide melting at 183°–187°.

The mixture of 1.0 g thereof, 12.4 g of freshly prepared silver carbonate, 58 ml of tetrahydrofuran and 10 ml of water is refluxed for 2 days in the absence of light, filtered and evaporated. The residue is taken up in ethyl acetate, the solution washed with water, dried and evaporated. The residue is chromatographed on silica gel and eluted with chloroform ethylacetate (9:1) to yield the N-(4-nitro-2-hydroxymethylphenyl)-4-chlorophthalimide.

EXAMPLE 14

The mixture of 1.7 g of N-(4-nitro-o-tolyl)-5-chlorohomophthalimide, 0.8 g of Raney nickel and 250 ml of ethyl acetate is hydrogented at 2.4 atm. and room temperature until the hydrogen uptake has ceased. It is filtered, the filtrate evaporated and the residue recrystallized from acetonitrile to yield the N-(4-amino-o-tolyl)-5-chlorohomophthalimide of the formula

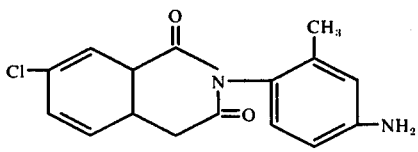

melting at 250°-252° with decomposition.

The starting material is prepared as follows. The mixture of 6.2 g of 5-chlorohomophthalic acid and 70 ml of acetic anhydride is refluxed for ½ hour and evaporated. The residue is washed with chloroform, carbon tetrachloride and dryed to yield the 5-chlorohomophthalic anhydride melting at 170°-173°.

The mixture of 3.6 g thereof, 2.7 g of 4-nitro-o-toluidine and 80 ml of toluene is refluxed for 4 days, cooled and filtered to yield the 2-(4-nitro-o-tolylcarbamoyl)-4-chlorophenylacetic acid melting at 238°-240°.

The suspension of 5.2 g thereof in 200 ml of chloroform is treated with an excess of ethereal diazomethane at 0° while stirring overnight at room temperature. The excess diazomethane is removed with a stream of nitrogen and the mixture filtered, to yield the corresponding methyl ester melting at 189°-192°. The solution of 3.6 g thereof in 60 ml of methanol is treated with a solution of 1.1 g of potassium t-butoxide in 70 ml of methanol while stirring under nitrogen. After 24 hours it is evaporated, the residue treated with water and acidified with N hydrochloric acid. The resulting precipitate is collected and recrystallized from ethyl acetate-diethyl ether to yield the N-(4-nitro-o-tolyl)-5-chlorohomophthalimide melting at 193°-203°.

EXAMPLE 15

The mixture of 1.55 g of N-(4-nitro-o-tolyl)-thiophene-2,3-dicarboximide, 0.7 g of Raney nickel and 180 ml of ethyl acetate is hydrogenated at 2.7 atm. and room temperature until the hydrogen uptake ceases. It is filtered, evaporated and the residue recrystallized from ethyl acetate-diethyl ether to yield the N-(4-amino-o-tolyl)-thiophene-2,3-dicarboximide melting at 237°-240°.

The starting material is prepared as follows: The mixture of 47.5 g of 3-cyano-thiophene-2-carboxylic acid, 700 ml of glacial acetic acid and 700 ml of conc. hydrochloric acid is refluxed for 3 hours, concentrated and filtered. The residue is dissolved in aqueous ammonium hydroxide, the mixture filtered, the filtrate reacidified with hydrochloric acid and the resulting thiophene-2,3-dicarboxylic acid collected, melting over a broad range of 235°-273° (indicative of decomposition).

The mixture of 17.2 g thereof and 125 ml of acetic anhydride is refluxed for 2½ hours, evaporated and the residue dryed by azeotropic distillation with toluene, to yield the thiophene-2,3-dicarboxylic anhydride. The mixture of 16 g thereof, 15.2 g of 4-nitro-o-toluidine and 125 ml of glacial acetic acid is refluxed for ½ hour, cooled, filtered and the residue washed with ethanol and diethyl ether, to yield the corresponding amide-acid melting at 245°-248°.

The mixture of 1.85 g thereof and 30 ml of acetic anhydride is refluxed for 5½ hours and evaporated. The residue is washed with ethanol and diethyl ether, dried and recrystallized from ethyl acetate, to yield the N-(4-nitro-o-tolyl)-thiophene-2,3-dicarboximide melting at 192°-194°.

EXAMPLE 16

The mixture of 2.5 g of N-(4-nitro-o-tolyl)-pyridine-3,4- dicarboximide, 1.2 g of Raney nickel and 575 ml of ethyl acetate is hydrogenated at 3.4 atm. and room temperature until the hydrogen uptake ceases. It is filtered, evaporated and the residue thoroughly leached with hot benzene. The filtrate is evaporated, the residue chromatographed on silica gel and eluted with ethyl acetate, to yield the N-(4-amino-o-tolyl)-pyridine-3,4-dicarboximide as an oil, the mass spectrum of which shows the expected molecular ion of 253.

The starting material is prepared as follows: The mixture of 12.0 g of pyridine-3,4-dicarboxylic acid and 60 ml of acetic anhydride is refluxed for 3 hours and evaporated. The residue is refluxed with 10.9 g of 4-nitro-o-toluidine and 350 ml of xylene for 48 hours, the mixture cooled and filtered. The residue is taken up in 400 ml of acetic anhydride, the solution refluxed for 6 hours and evaporated. The residue is recrystallized from ethyl acetate with the aid of decolorizing carbon, to yield the N-(4-nitro-o-tolyl)-pyridine-3,4-dicarboximide melting at 187°-189°.

EXAMPLE 17

The solution of 416 g of N-(4-nitro-o-tolyl)-4-chlorophthalimide in 28 lt. of hot ethyl acetate is cooled slightly and transferred under nitrogen to 250 ml (or 460 g) of a suspension of Raney nickel, which has been washed 4 times with anhydrous ethanol and 1 times with ethyl acetate, and 12 lt of ethyl acetate are used for the rinse. The mixture is hydrogenated at 3.4 atm. and 30° for approximately 8 hours, and continued for 2 hours after the hydrogen uptake has ceased. It is filtered, the residue rinsed with 15 lt. of ethyl acetate and the filtrate concentrated to about 14 lt. It is cooled, filtered, and the filtrate reduced to approximately 1½ lt to yield 2 crops of N-(4-amino-o-tolyl)-4-chlorophthalimide melting at 205°-207°; it is identical (but somewhat purer) than that obtained according to Example 4.

The starting material is prepared as follows: The mixture of 9.0 g of 4-chloro-o-xylene and the solution of 60.7 g of potassium permanganate in 280 ml of water is refluxed until the purple color disappears (about 7 hours) whereupon ¾ of the water are distilled off and the remaining suspension is filtered while still hot. The residue is washed with hot water several times, the clear and colorless filtrate (pH∼12) is concentrated to about 50 ml and acidified with 33 ml of concentrated hydrochloric acid. The cold mixture is extracted 3 times with ethyl acetate, the organic layer dried and evaporated to give the 4-chlorophthalic acid.

The solution of 7.76 g thereof in 75 ml of acetic anhydride is refluxed for 2 hours and evaporated. The residue is sublimed at 88°/0.35 mm Hg and recrystalized from diethyl ether yield the 4-chloro-phthalic anhydride melting at 93° to 94°.

To the solution of 276 g thereof in 4.2 lt. of glacial acetic acid 230 g of 4-nitro-o-toluidine are added while stirring and the mixture is heated for 45 minutes until dissolution occurs. It is refluxed for 4 hours, cooled, filtered and the residue washed with diethyl ether, to yield the N-(4-nitro-o-tolyl)-4-chlorophthalimide melting at 227°-229°.

EXAMPLE 18

The solution of 1.0 g of N-(4-nitro-o-tolyl)-4-methoxyphthalimide in 70 ml of ethyl acetate is hydrogenated over 0.35 g of platinum oxide at 2.5 atm. and room temperature for 2 hours. It is filtered, the filtrate concentrated and the precipitate formed collected, to yield the N-(4-amino-o-tolyl)-4-methoxyphthalimide melting at 158°–161°.

The starting material is prepared as follows: The mixture of 2.0 g of 4-methoxyphthalic anhydride 1.7 g of 4-nitro-o-toluidine and 20 ml of acetic acid is refluxed for 4 hours, cooled in an ice-bath and filtered, to yield the N-(4-nitro-o-tolyl)-4-methoxyphthalimide melting at 170°–171°.

EXAMPLE 19

The solution of 4.0 g of N-(4-nitro-o-tolyl)-4-carboxyphthalimide in 200 ml of ethyl acetate is hydrogenated over 1.0 g of platinum oxide at 2.5 atm. and about 40° for 50 minutes. the suspension obtained is evaporated, the residue taken up in 50 ml of dimethylformamide, the mixture filtered, the filtrate evaporated and the residue triturated with 100 ml of ethanol, to yield the N-(4-amino-o-tolyl)-4-carboxyphthalimide melting at 280°. Analogousy the N-(4-amino-o-tolyl)-4-carbomethoxyphthalimide is prepared, melting after recrystallization from ethyl acetate-diethyl ether at 161°–162°.

The starting materials are obtained as follows: The mixture of 21.1 g of trimellitic anhydride, 16.7 g of 4-nitro-o-toluidine and 250 ml of acetic acid is refluxed for 22 hours, cooled in an ice-bath and filtered, to yield the N-(4-nitro-o-tolyl)-4-carboxyphthalimide melting at 262°–263°.

The stirred suspension of 4.0 g thereof in 100 ml of methylene chloride is treated with an excess of ethereal diazomethane at 0°, whereupon dissolution occurs After 10 minutes it is gassed with nitrogen, evaporated and the residue recrystallized from diethyl ether-hexane, to yield the N-(4-nitro-o-tolyl)-4-carbomethoxyphthalimide melting at 185°–187°.

EXAMPLE 20

The mixture of 1.5 g of N-(4-nitro-o-tolyl)-4-carbamoylphthalimide 200 ml of ethylacetate and 0.3 g of platinum oxide is hydrogenated at 2.5 atm. and about 40° for 50 minutes. It is filtered, the filtrate concentrated and the precipitate collected, to yield the N-(4-amino-o-tolyl)-4-carbamoylphthalimide melting at 240°–242°.

Analogously the N-(4-amino-o-tolyl)-4-cyanophthalimide is obtained after hydrogenation over Raney nickel at room temperature; it shows I.R.-bands at 3350, 2240, 1785 and 1725cm$^{-1}$ (in Nujol).

The starting materials are prepared as follows: The mixture of 10.9 g N-(4-nitro-o-tolyl)-4-carboxyphthalimide and 50 ml of thionyl chloride is refluxed for one hour, evaporated and the residue recrystallized from diethyl ether, to yield the corresponding acid chloride metling at 177°–179°.

To the solution of 2.7 g thereof in 50 ml of tetrahydrofuran, 50 ml of saturated ammonia in tetrahydrofuran are added dropwise while stirring at room temperature. The mixture is evaporated after 30 minutes, the residue slurried in 300 ml of methylene e chloride, filtered, the filtrate concentrated to about 2 ml and the precipitate collected, to yield the N-(4-nitro-o-tolyl)-4-carbamoylphthalimide melting at 229°–230°.

The mixture of 2.0 g thereof and 50 ml of phosphorus oxychloride is refluxed for 2 hours, evaporated, the residue slurried in 20 ml of diethyl ether and filtered off, to yield the N-(4-nitro-o-tolyl)-4-cyanophthalimide melting at 239°–240°.

EXAMPLE 21

The mixture of 0.3 g of N-(4-amino-o-tolyl)-4-carbamoylphthalamide, 2 ml of dioxane and 5 ml of phosphorus oxychloride is refluxed for 1 hour and evaporated. The residue is taken up in methylene chloride, the solution washed with cold aqueous sodium carbonate, dried and evaporated, to yield the N-(4-amino-o-tolyl)-4-cyanophthalimide, which is identical with that obtained according to Example 20.

EXAMPLE 22

The solution of 0.5 g of N-(4-nitro-o-tolyl)-4-chloro-α-methylhomophthalimide in 120 ml of ethyl acetate is hydrogenated over 2.0 g of Raney nickel (washed with water and ethanol) at 2.5 atm. and room temperature for 5 hours. It is filtered and the filtrate evaporated, to yield the N-(4-amino-o-tolyl)-4-chloro-α-methylhomophthalimide of the formula

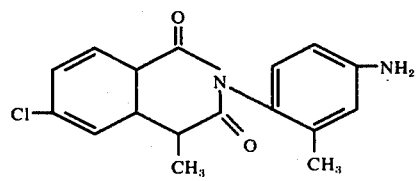

showing in the I.R.-spectrum bands at 1665 and 1710cm$^-$ and in the mass-spectrum the ion of 314/316.

The starting material is prepared as follows: To the ice-cooled, stirred solution of 9.6 ml of diisopropylamine in 200 ml of tetrahydrofuran, 42 ml of 1.6 molar butyl lithium in hexane are slowly added, followed by the solution of 5.1 g of 4-chloro-2-methylbenzoic acid in 60 ml of tetrahydrofuran. The mixture is stirred for 15 minutes at 0°, then cooled to −70° and 7.5 ml of methyl iodide are slowly added. It is allowed to warm to 0°, quenched with water, the aqueous layer separated and acidified with concentrated hydrochloric acid. It is extracted with methylene chloride, the extract dried and evaporated, to yield the 4-chloro-2-ethylbenzoic acid.

To the ice-cooled solution of 8.3 ml of diisopropylamine in 150 ml of tetrahydrofuran, 36ml of 1.6 molar butyl lithium in hexane are slowly added, followed by the solution of 4.6 g of 4-chloro-2-ethylbenzoic acid in 70 ml of tetrahydrofuran. The mixture is stirred for 15 minutes at 0°, then cooled to −40° and 4.1 ml of t.-butylisocyanate are added at once. It is allowed to warm to room temperature, quenched with water, the aqueous layer separated and acidified with concentrated hydrochloric acid. It is extracted with methylene chloride, the extract dried, evaporated and the residue triturated with diethyl ether, to yield the N-t-butyl-α-(2-carboxy-5-chlorophenyl)-propionic acid amide melting at 175°–178°.

The solution of 2.1 g thereof in 40 ml of dioxane and 40 ml of 5 N hydrochloride acid is refluxed for 16 hours, evaporated and the residue recrystallized from ethyl acetate, to yield the corresponding free diacid melting at 151°–153°.

The mixture of 0.9 g thereof, 4 ml of acetyl chloride and 25 ml of dioxane is stirred for 20 minutes at 65° and evaporated. The residue is taken up in 60 ml of toluene, 0.61 g of 4-nitro-o-toluidine are added, the mixture refluxed for 15 hours on a water-trap and evaporated, to yield the N-(4-nitro-o-tolyl)-α-(2-carboxy-5-chlorophenyl)-propionic acid amide.

The ice-cooled suspension of 1.5 g thereof in 100 ml of diethyl ether is treated with an excess of ethereal diazomethane until no further nitrogen evolves. It is evaporated, the residue taken up in 50 ml of methanol and 0.45 g of potassium t.-butoxide in 10 ml of methanol are added. The mixture is stirred for 12 hours at room temperature, evaporated and the residue taken up in ethyl acetate. The solution is washed with aqueous monosodium phosphate, dried and evaporated, to yield the N-(4-nitro-o-tolyl)-4-chloro-α-methyl-homophthalimide.

EXAMPLE 23

Preparation of 10,000 tablets each containing 100.0 mg of the active ingredient:

| Formula: | |
|---|---|
| N-(4-amino-o-tolyl)-4-chlorophthalimide | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

In the analogous manner tablets are prepared, containing any of the other compounds of the invention, preferably those illustrated by the preceding examples herein.

EXAMPLE 24

The mixture of 0.5 g of N-(4-isocyanato-o-tolyl)-4-chlorophthalimide, 25 ml of p-dioxane and 10 ml of N hydrochloric acid is refluxed for 30 minutes and evaporated. The residue is taken up in methylene chloride, the solution washed with cold 5% aqueous sodium carbonate, dried, evaporated and the residue recrystallized from ethyl acetate, to yield the N-(4-amino-o-tolyl)-4-chlorophthalimide melting at 202°–204°.

The starting material is prepared as follows: The suspension of 6.0 g of 4-chlorophthalic anhydride, 5.0 g of 4-amino-3-methylbenzoic acid and 75 ml of acetic acid is refluxed for 3 hours, cooled to room temperature, filtered and the residue washed with diethyl ethyl, to yield the N-(4-carboxy-o-tolyl)-4-chlorophthalimide melting at 250°–252°.

To the solution of 2.52 g thereof in 16 ml of acetone, 1.6 ml of water and 1.22 ml of triethylamine, 0.88 ml of ethyl chloroformate are added while stirring and cooling with ice. After 30 minutes the solution of 0.725 g of sodium azide in 2 ml of water is added and stirring is continued for 1 hour at 0°. The mixture is evaporated, the residue taken up in methylene chloride, the solution washed with water, dried and evaporated, to yield the N-(4-azidocarbonyl)-4-chlorophehalimide melting at 134°–136°.

The solution of 2.7 g thereof in 100 ml of toluene is refluxed for 4 hours, cooled to room temperature, filtered and the filtrate evaporated, to yield the N-(4-isocyanato-o-tolyl)-4-chlorophthalimide melting at 176°–178°.

EXAMPLE 25

The mixture of 0.75 g of N-(4-benzyloxycarbonylamino-o-tolyl)-4-chlorophthalimide 100 ml of ethyl acetate and 0.1 g of 10% palladium on charcoal is hydrogenated at 2.5 atm. and room temperature for 4 hours whereby the intermediarily formed carbaminic acid decarboxylates. The mixture is filtered, the filtrate concentrated to 10 ml and the precipitate formed collected, to yield the N-(4-amino-o-tolyl)-4-chlorophthalimide melting at 202°–204°.

The starting material is prepared as follows: The mixture of 0.5 g of N-(4-isocyanato-o-tolyl)-4-chlorophthalimide and 5ml of benzyl alcohol is heated to 120° under nitrogen for 6 hours and evaporated, to yield the N-(4-benzyloxycarbonylamino-o-tolyl)-4-chlorophthalimide.

EXAMPLE 26

The mixture of 0.6 g of N-(4-t.butoxycarbonylamino-o-tolyl)-4-chlorophthalimide and 5 ml of trifluoroacetic acid is refluxed for 2 hours and evaporated. The residue is taken up in methylene chloride, the solution washed with 5% aqueous sodium bicarbonate, dried, evaporated and the residue recrystallized from ethyl acetate, to yield the N-(4-amino-o-tolyl)-4-chlorophthalimide melting at 203°–204°.

The starting material is prepared as follows: The mixture of 0.5 g of N-(4-isocyanato-o-tolyl)-4-chlorophthalimide and 10 ml of freshly distilled, dry tert. butanol is refluxed under nitrogen for 24 hours and evaporated, to yield the N-(4-t.butoxy-carbonylamino-o-tolyl)-4-chlorophthalimide.

EXAMPLE 27

The solution of 1.65 g of N-(2-ethyl-4-nitrophenyl)-4-chlorophthalimide in 80 ml of ethyl acetate is hydrogenated over 5 g of Raney Nickel at 2.5 atm. of hydrogen pressure for 5 hours. After filtration the residue of 1.5 g is crystallized from ethyl acetate-hexane to give 800 mg of the N-(2-ethyl-4-aminophenyl)-4-chlorophthalimide melting at 118°–120°.

The starting material is prepared as follows: The solution of 3.6 g of 3-chlorophthalic anhydride, 3.3 g of 2-ethyl-4-nitroaniline [L. Kirch et al, J. Org. Chem. 21, 1309 (1956)] and 55 ml of glacial acetic acid is refluxed for 4 hours. After cooling to room temperature, it is filtered and 4.6 g of crystalline N-(2-ethyl-4-nitrophenyl)-4-nitrophenyl)-4-chlorophthalimide are collected, m.p. 147°–148°.

We claim:
1. An N-(4-aminophenyl)-aromatic dicarboximide corresponding to the formula

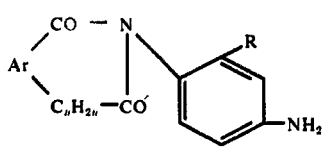

wherein Ar is 1,2-phenylene substituted by one member selected from lower alkyl, lower alkoxy, lower alkylmercapto, lower alkyl sulfinyl, lower alkylsulfonyl, halogeno, trifluoromethyl, carboxy, lower carbalkoxy, cyano, carbamoyl, sulfamoyl, mono- or di-lower alkylcarbamoyl, mono- or di-lower alkylsulfamoyl R is lower alkyl, (hydroxy, lower alkoxy, lower alkylmercapto, lower alkylsulfinyl or lower alkylsulfonyl)-lower alkyl, halogeno or trifluoromethyl, $n$ is an integer from 1 to 3 and $C_nH_{2n}$ separates Ar from CO by at least one carbon atom, or pharmaceutically acceptable salts thereof.

2. A compound as claimed in claim 1, in which formula Ar is 1,2-phenylene substituted by one member selected from lower alkyl, lower alkoxy, lower alkylmercapto, lower alkylsulfinyl, lower alkylsulfonyl, halogeno, trifluoromethyl, carboxy, lower carbalkoxy, cyano, carbamoyl, sulfamoyl, mono- or di-lower alkylcarbamoyl, mono- or di-lower alkylsulfamoyl R is lower alkyl, lower α-(hydroxy, lower alkoxy, lower alkylmercapto, lower alkylsulfinyl or lower alkylsulfonyl)-lower alkyl, halogeno or trifluoromethyl and $n$ is the integer 1, or a therapeutically acceptable alkali metal or acid addition salt thereof.

3. A compound as claimed in claim 1, in which formula Ar is 1,2-phenylene substituted by one member selected from methyl, ethyl, methoxy, ethoxy, (methyl or ethyl)-(mercapto, sulfinyl or sulfonyl), fluoro, chloro, bromo, trifluoromethyl, carboxy, carbomethoxy, cyano, carbamoyl, sulfamoyl, mono or di-(methyl or ethyl)-(carbamoyl or sulfamoyl); R is methyl, ethyl, fluoro, chloro, bromo, trifluoromethyl or α-(hydroxy, methoxy, ethoxy, methyl- or ethylmercapto, -sulfinyl or -sulfonyl)-(methyl or ethyl) and $n$ is the integer 1, or a therapeutically acceptable acid addition salt thereof.

4. A compound as claimed in claim 1 and corresponding to the formula

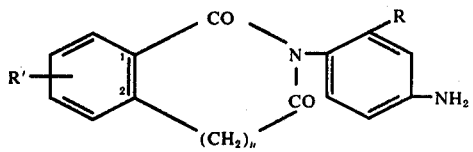

wherein R is methyl or ethyl, R' is methyl, methoxy, methylmercapto, methylsulfinyl, methylsulfonyl, fluoro, chloro, bromo, trifluoromethyl, carboxy, cyano, carbamoyl or dimethylcarbamoyl and $n$ is the integer 1, or a therapeutically acceptable acid addition salt thereof.

5. A compound as claimed in claim 4, wherein R' is in the 4- or 5-positions.

6. A compound as claimed in claim 1, in which formula Ar is 4-chloro-1,2-phenylene, R is methyl and $C_nH_{2n}$ is ethylidene.

7. A compound as claimed in claim 4 and being the N-(4-amino-o-tolyl)-5-chlorohomophthalimide.

* * * * *